(12) United States Patent
Henneberg et al.

(10) Patent No.: US 9,380,942 B2
(45) Date of Patent: Jul. 5, 2016

(54) APPARATUS FOR NON-INVASIVE IN VIVO MEASUREMENT BY RAMAN SPECTROSCOPY

(75) Inventors: Morten Henneberg, Odense M (DK); Stefan Ovesen Banke, Nyborg (DK); Anders Weber, Copenhagen (DK)

(73) Assignee: RSP SYSTEMS A/S, Odense S. (DK)

( * ) Notice: Subject to any disclaimer, the term of this patent is extended or adjusted under 35 U.S.C. 154(b) by 196 days.

(21) Appl. No.: 13/542,462

(22) Filed: Jul. 5, 2012

(65) Prior Publication Data
US 2013/0018237 A1 Jan. 17, 2013

Related U.S. Application Data

(63) Continuation-in-part of application No. PCT/EP2011/050059, filed on Jan. 4, 2011.

(30) Foreign Application Priority Data

Jan. 7, 2010 (GB) .................................. 1000179.0

(51) Int. Cl.
| | |
|---|---|
| A61B 5/1455 | (2006.01) |
| A61B 5/00 | (2006.01) |
| A61B 5/145 | (2006.01) |
| A61B 5/1495 | (2006.01) |
| G01N 21/65 | (2006.01) |

(52) U.S. Cl.
CPC .............. *A61B 5/0075* (2013.01); *A61B 5/0059* (2013.01); *A61B 5/0068* (2013.01); *A61B 5/14532* (2013.01); *A61B 5/441* (2013.01); *A61B 5/1495* (2013.01); *A61B 2562/0242* (2013.01); *A61B 2562/146* (2013.01); *G01N 21/65* (2013.01)

(58) Field of Classification Search
CPC ....................................................... A61B 5/1455
USPC .................................................. 600/310–344
See application file for complete search history.

(56) References Cited

U.S. PATENT DOCUMENTS

| | | |
|---|---|---|
| 5,553,616 A | 9/1996 | Ham et al. |
| 5,615,673 A | 4/1997 | Berger et al. |
| 5,842,995 A | 12/1998 | Mahadevan-Jansen et al. |

(Continued)

FOREIGN PATENT DOCUMENTS

| | | |
|---|---|---|
| JP | 2002-224091 | 8/2002 |
| JP | 2008-509728 | 4/2008 |

(Continued)

OTHER PUBLICATIONS

International Search Report mailed May 3, 2011 in corresponding International Patent Application No. PCT/EP2011/050059.

(Continued)

*Primary Examiner* — Eric Winakur
*Assistant Examiner* — Marjan Fardanesh
(74) *Attorney, Agent, or Firm* — Pillsbury Winthrop Shaw Pittman LLP

(57) ABSTRACT

A metabolite concentration is measured in vivo using Raman spectroscopy in such a way as to receive at a detector (229) light scattered from the metabolite in interstitial fluid in skin in a measurement location (217) at a depth (218) of from 200-300 µm below the skin surface providing improved retention of correct calibration and transferability of calibration between individual subjects.

7 Claims, 9 Drawing Sheets

(56) References Cited

U.S. PATENT DOCUMENTS

| | | | |
|---|---|---|---|
| 6,167,290 | A | 12/2000 | Vang et al. |
| 6,310,686 | B1 | 10/2001 | Jiang |
| 7,277,210 | B2 | 10/2007 | Lipson |
| 7,742,166 | B2 | 6/2010 | Lipson et al. |
| 7,973,925 | B2 | 7/2011 | Lipson et al. |
| 8,027,033 | B2 | 9/2011 | Lipson et al. |
| 2005/0036147 | A1 | 2/2005 | Sterling et al. |
| 2005/0117150 | A1 | 6/2005 | Puppels et al. |
| 2006/0063991 | A1* | 3/2006 | Yu ................ A61B 5/14532 600/322 |
| 2006/0135861 | A1* | 6/2006 | Lucassen et al. ............ 600/315 |
| 2006/0234386 | A1 | 10/2006 | Burns et al. |
| 2008/0129992 | A1 | 6/2008 | Matousek et al. |
| 2010/0226549 | A1 | 9/2010 | Smous et al. |

FOREIGN PATENT DOCUMENTS

| | | | |
|---|---|---|---|
| JP | 2008-289807 | | 12/2008 |
| WO | 97/36540 | | 10/1997 |
| WO | 99/27848 | | 6/1999 |
| WO | 00/02479 | | 1/2000 |
| WO | 01/39665 | | 6/2001 |
| WO | 02/07585 | | 1/2002 |
| WO | 02/057759 | | 7/2002 |
| WO | 2004/055473 | | 7/2004 |
| WO | 2004/082474 | | 9/2004 |
| WO | 2005/012553 | | 2/2005 |
| WO | 2005/019803 | | 3/2005 |
| WO | 2005/112590 | | 12/2005 |
| WO | 2006/012514 | | 2/2006 |
| WO | 2006/020408 | | 2/2006 |
| WO | 2006/059226 | | 6/2006 |
| WO | 2006/127766 | | 11/2006 |
| WO | 2006/131119 | | 12/2006 |
| WO | 2007/014173 | | 2/2007 |
| WO | 2007/127909 | | 11/2007 |
| WO | 2007/147164 | | 12/2007 |
| WO | 2008/052221 | | 5/2008 |
| WO | 2008/098049 | A2 | 8/2008 |
| WO | 2008/098049 | A3 | 8/2008 |
| WO | 2009/149266 | | 12/2009 |
| WO | 2010/013264 | | 2/2010 |
| WO | 2010/102621 | | 9/2010 |
| WO | 2010/135700 | | 11/2010 |
| WO | 2010/141258 | | 12/2010 |
| WO | 2010/141262 | | 12/2010 |
| WO | 2011/083111 | | 7/2011 |
| WO | 2011/097310 | | 8/2011 |

OTHER PUBLICATIONS

Alan G. Ryder et al., "Quantitative analysis of cocaine in solid mixtures using Raman spectroscopy and chemometric method," J. Raman Spectrosc., vol. 31, pp. 221-227 (2000).

Igor V. Ermakov, "Resonance Raman detection of carotenoid antioxidants in living human tissues," Optics Letters, vol. 26, No. 15, pp. 1179-1181 (Aug. 1, 2001).

Annika M.K. Enejder et al., "Raman spectroscopy for noninvasive glucose measurements," J. Biomedical Optics, vol. 10, No. 3, pp. 031114-1-031114-9 (May/Jun. 2005).

Jonathon T. Olesberg et al., "In vivo near-infrared spectroscopy of rat skin tissue with varying blood glucose levels," Proc. of SPIE, vol. 5325, pp. 11-20 (2004).

J, Chaiken et al., "Noninvasive in vivo tissue and pulse modulated Raman spectroscopy of human capillary blood and plasma," Proc. of SPIE, vol. 6093, pp. 609305-1-609305-11 (2006).

P.J. Caspers et al., "Combined in Vivo Confocal Raman Spectroscopy and Confocal Microscopy of Human Skin," Biophysical Journal, vol. 85, pp. 572-580 (Jul. 2003).

Fabiano de Barros Souza et al., "Intramuscular lactic acid assessment through Raman spectrography: new perspectives in sports medicine," Rev. Bras. Med. Esporte, vol. 9, No. 6, pp. 396-402 (Nov./Dec. 2003).

Igor V. Ermakov, "Resonance Raman detection of carotenoid antioxidants in living human tissues," J. Biomed Opt., vol. 10, No. 6, pp. 1-35 (May 3, 2011).

T. Scecina et al., "Raman spectroscopy for measurement of blood analytes," MIT Spectroscopy-Research in Biomedical Optics, http://web.mit.edu/spectroscopy/research/biomedresearch, pp. 1-5 (printed Jun. 6, 2012).

Urs Utzinger et al., "Fiber optic probes for biomedical optical spectroscopy," J. Biomedical Optics, vol. 8, No. 1, pp. 121-147 (Jan. 2003).

Japanese Office Action mailed Apr. 4, 2014 in corresponding Japanese Patent Application No. 2012-547500.

* cited by examiner

APPARATUS FOR NON-INVASIVE IN VIVO MEASUREMENT BY RAMAN SPECTROSCOPY

RELATED APPLICATIONS

This is a continuation in part of PCTEP2011/050059 filed 4 Jan. 2011 and claims priority from that and from GB 1000179.0 filed 7 Jan. 2010.

The invention relates to apparatus for non-invasive in vivo measurement by Raman spectroscopy of glucose and other compounds including lactate present in interstitial fluid in skin.

BACKGROUND

Spectroscopy is a method for obtaining information on a molecular scale by the use of light. This information can be related to the rotational, vibrational and/or electronic states of the molecules probed as well as dissociation energy and more. The rotational and/or vibrational spectrum of a given molecule is specific for that molecule. As a consequence, molecular spectra in particular rotation and/or vibrational spectra are often referred to as 'fingerprints' related to a specific molecule. Information related to rotational, vibrational and/or electronic states of molecules can therefore be used to analyze a sample comprising a number of unknown molecular components, thereby obtaining knowledge about the molecular components in the sample.

The basis for a spectroscopic setup is a light source, e.g. a laser, which is used for illuminating a sample. The light from the light source (the incoming light) will interact with the sample, and often result in an alternation of the light which is transmitted through, emitted by, reflected by and/or scattered by the sample. By collecting the altered light and analyzing its spectral distribution, information about the interaction between the incoming light and the molecular sample can be obtained; hence information about the molecular components can be obtained.

The spectral distribution is typically measured by using a spectrometer. A spectrometer is an optical apparatus that works by separating the light beam directed into the optical apparatus into different frequency components and subsequently measuring the intensity of these components by using e.g. a CCD detector, a CCD array, photodiode or such.

The altered light reflecting interactions between the incoming light and the molecular sample can roughly be characterized as either emission or scattering. The emission signals have relatively broad spectral profiles as compared to scattering light signals, which normally display quite narrow spectral lines. One process often dominates over the other, but both processes can and most often will occur simultaneously. The intensity of the emitted light vs. the intensity of the scattered light depends among other things on the frequency and the power of the incoming light, the intensity of the incoming light at the measuring point in the sample, and the molecular components in the sample.

Scattered light can be classified as being either elastic or inelastic and these are characterized by being spectroscopically very narrow signals. Elastic scattering is referred to as Rayleigh scattering, in which there is no frequency shift. Rayleigh scattering thus has the same frequency as that of the incoming light.

The most commonly known example of inelastic scattering is Raman scattering, in which there is an energy interchanging between the molecule and the photons of the incoming light. The frequencies, i.e. the spectral distribution of the Raman scattered light will be different from that of the incoming light and uniquely reflect the specific vibrational levels of the molecule; hence it is a fingerprint spectrum. This can be used for identification of the molecular composition of the substance probed and/or the concentration of the specific molecules in the substance.

Raman scattering is a relatively weak process compared to e.g. Rayleigh scattering and fluorescence. Reduction of contributions from these other processes is thus desirable when collecting Raman scattered light. In addition, the intensity of the Raman scattered light depends strongly on the frequency and the intensity of the incoming light. If these are variable, it may therefore be essential to monitor power fluctuations in the incoming light if one is to receive reliable information about the distribution of molecular components in different samples and/or sample spot bases on analysis of the collected Raman scattered light, depending on the precision needed. The same is true if the analysis of the molecular components in a sample and/or different sample spots is bases on emission spectra.

Skin comprises a number of layers having different characteristics and containing different kinds of cells and structures. Various proposals for using Raman spectroscopy to measure glucose in skin or in other parts of the body have been made, but none of these has to date provided a system which can be used on most candidate subjects without adjustment to suit a particular individual and without calibration for that individual. It is thereby possible to calibrate an instrument against measurements of blood glucose concentration made on one individual or a group of individuals by other means such as chemical analysis and to apply that same calibration when the instrument is used on other individuals than the one or ones involved in the calibration. We have now appreciated that the key to achieving such a result is to ensure that the Raman scattered light that is collected for measurement originates at or close to a specific depth within the skin.

Caspers et al; Biophysical Journal, Vol 85, July 2003, describes an in vivo confocal Raman spectroscopy method and apparatus which is said to be useful for measuring glucose. It contains however no instruction as to the depth from which the Raman scattering should be collected in a glucose measurement and there is a strong suggestion deducible from the teaching that the apparatus had not actually been tried for this purpose.

WO2008/052221 describes a method and apparatus for coherent Raman spectroscopy that transmits light through a sample surface such as skin and tissue to a focal plane within the sample to measure for instance glucose. However, no teaching is present of the importance of selecting a particular depth for the focal plane or where this should be. Indeed, it is specifically acknowledged that using the described apparatus variations in the detected signal occur when the analyte concentration is constant due to effects of skin temperature and hydration. No suggestion is present that such effects can be avoided by a careful selection of the depth from which the measurements are taken.

WO97/36540 describes determination of the concentration of e.g. glucose using Raman spectroscopy and an artificial neural network discriminator. However, the Raman signals are not selectively obtained from a particular depth and the need to compensate for non-linearities arising from signals penetrating to a depth of >500 µm is discussed.

WO00/02479 discloses a method and apparatus for non-invasive glucose measurement by confocal Raman spectroscopy of the aqueous humor of the anterior chamber of the eye. Naturally, there is no teaching of a depth at which to make optimal measurements in skin.

WO2009/149266 refers back to Ermakov I V, Ermakova M R, McClane R W, Gellermann W. Opt Lett. 2001 Aug. 1; 26(15):1179-81, 'Resonance Raman detection of carotenoid antioxidants in living human tissues.' which describes using resonance Raman scattering as a novel noninvasive optical technology to measure carotenoid antioxidants in living human tissues of healthy volunteers. By use of blue-green laser excitation, clearly distinguishable carotenoid Raman spectra superimposed on a fluorescence background are said to be obtained.

Chaiken et al (Noninvasive blood analysis by tissue modulated NIR Raman spectroscopy, J. Chaiken et. al., Proc. of SPIE optical Eng., 2001, vol. 4368, p. 134-145) obtained a correlation of only 0.63 between Raman based measurements and fingerstick blood glucose measurements across several individuals, but were able to obtain a correlation of 0.90 for a single individual. The setup utilized by Chaiken et al comprises a collimated excitation beam and so naturally do not disclose any optimal focal depth.

WO2006/127766, WO02/07585 and US2006/0234386 all describe the use of Raman spectroscopy for measuring lactate through the skin surface. Lactate measurements may be used for various purposes including monitoring the effect of exercise and determining whether a person has died or is still living. In critical care, the monitoring of blood lactate is of importance. High levels of lactate may be associated with myocardial infarction, cardiac arrest, circulatory failure and emergency trauma situations.

The present invention now provides apparatus for non-invasive in vivo measurement by Raman spectroscopy of a substance, especially but not exclusively lactate or glucose but also including fatty acids, urea, carbamide, cholesterol and hemoglobin, present in interstitial fluid in the skin of a subject, comprising a light source, optical components defining a light path from said light source to a measurement location, a light detection unit, optical components defining a return path for Raman scattered light from said measurement location to said light detection unit, and a skin engaging member having a distal surface for defining the position of said optical components defining the return path with respect to a surface of said skin in use, and wherein said optical components defining a light path from said light source to a measurement location beneath the surface of the skin focus the light emitted from said light source to a depth located at from 200 to 300 µm beneath the surface of the skin and optical components defining a return path for Raman scattered light selectively transmit to said light detection unit light scattered from near said measurement location such that at least 50% of Raman scattered light received at the light detection unit originates at depths from 60 to 400 µm beyond said distal surface of the skin engaging member.

The apparatus may include means for computing a concentration of a substance, particularly a metabolite, in interstitial fluid or blood based on analysis of said Raman scattered light. Metabolites may be glucose or lactate in particular, but also fatty acids, urea, carbamide, cholesterol, or hemoglobin. The Raman spectrum may be analysed by application thereto of a trained statistical model which relates peak intensities to the relevant metabolite concentration. This may be performed using partial least squares regression (PLS) as described in more detail in the references acknowledged in M. A. Arnold; In Vivo Near-Infrared Spectroscopy of Rat Skin Tissue with Varying Blood Glucose Levels; Anal. Chem. 2006, 78, 215-223 therein and in A. M. K. Enejder et al; Raman Spectroscopy for Non-invasive Glucose Measurements; Jnl of Biomedical Optics, 10(3), 031114; May/June 2005. Other forms of multivariate calibration may be used including Principal Component Analysis (PCA) in a manner analogous to that described in for instance A. G. Ryder, G. M. Connor and T. J. Glynn; Quantitative Analysis of Cocaine in Solid Mixtures using Raman Spectroscopy and Chemometric Methods; Journal of Raman Spectroscopy, 31; 221-227 (2000) or in J. T. Olesberg, L. Liu, V. V. Zee, and M. A. Arnold; In Vivo Near-Infrared Spectroscopy of Rat Skin Tissue with Varying Blood Glucose Levels; Anal. Chem. 2006, 78, 215-223. In general, statistical methods of spectrum analysis useful in calibrating detection of analytes from absorption spectra will be useful in analysis of Raman spectra also.

Preferably, said percentage is at least 55%. Preferably also, at least 90% of Raman scattered light received at the light detection unit originates at depths less than 600 µm beyond said distal surface of the skin engaging member. On the other hand, preferably less than 25% of Raman scattered light received at the light detection unit originates at depths less than 100 µm beyond said distal surface of the skin engaging member.

Preferably, at least 15% of Raman scattered light received at the light detection unit originates at depths from 200 to 300 µm beyond said distal surface of the skin engaging member.

Said optical components preferably defining a light path from said light source to a measurement location beneath a surface of skin preferably focus the light emitted from said light source to a depth located at from 210 to 300 µm, e.g. 250 beneath the surface of the skin.

In an alternative aspect, the invention provides apparatus of the kind described for measuring the concentration of a metabolite in interstitial fluid, wherein said Raman scattered light received at said detection unit includes at least light scattered by glucose or light scattered by lactate.

Apparatus according to the invention may comprise a hand piece for application to the skin containing components defining said measurement location in use, and one or more optical fibres connecting said hand piece to said light source and to a processing unit containing electronic circuitry for analysis of signals received from said light detection unit to provide said measurement therefrom.

The position distal of the skin engaging member of said measurement location is optionally adjustable and can be adjusted to be from 60 to 400 µm beyond said distal surface of the skin engaging member or can be adjusted to be from 200 (or 210) to 300 µm, beneath the surface of the skin. Alternatively, however the position distal of the skin engaging member of said measurement location is fixed, suitably such that the numerical parameters discussed above are achieved.

Thus, the depth of focus of the optical components defining said light path, and/or the optical components defining said return path may be fixed rather than adjustable.

The invention includes a method for non-invasive in vivo measurement by Raman spectroscopy of a said substance present in interstitial fluid in the skin of a subject, comprising directing light from a light source into the skin of said subject via optical components defining a light path from said light source to a measurement location in the skin, receiving Raman scattered light back from the skin at a light detection unit via optical components defining a return path for Raman scattered light from said measurement location to said light detection unit, whilst using a skin engaging member having a distal surface for defining the position of said optical components defining the return path with respect to a surface of said skin in use, and wherein said optical components defining a light path from said light source to a measurement location beneath a surface of skin focus the light emitted from said light source to a depth located at from 200 to 300 µm beneath the surface of the skin and said optical components defining a return path for Raman scattered light selectively transmit to said light detection unit light scattered from near said measurement location such that at least 50% of Raman scattered light received at the light detection unit originates at depths from 60 to 400 μm beyond said distal surface of the skin engaging member. The method is preferably performed using apparatus in accordance with the invention.

The method may include calibrating the output of the apparatus by the use of the apparatus to provide an output in respect of a known metabolite concentration prior to said measurement on said subject. Once calibrated the apparatus preferably is not calibrated again for a period of not less than a week, more preferably a month. Preferably, said calibration step of providing an output in respect of a known metabolite concentration is not carried out by the use of the apparatus on said subject.

Thus, the calibration may be conducted on a different subject for whom a blood glucose concentration or lactate or other metabolite concentration is known or may be conducted using a standard reference material such as a drop of metabolite solution placed in the measurement location or a solid phantom simulating a metabolite solution.

Any apparatus described herein may be used in such a method.

The invention further includes a handpiece for use in apparatus according to claim 1, said handpiece containing optical components defining a light path for light received at said handpiece from a light source to communicate said light to a measurement location, optical components defining a return path for Raman scattered light from said measurement location and for communicating said Raman scattered light to a remote light detection unit, and a skin engaging member having a distal surface for defining the position of said optical components defining the return path with respect to a surface of said skin in use, and wherein said optical components defining a light path from said light source to a measurement location beneath a surface of skin focus the light emitted from said light source to a depth located at from 200 to 300 μm beneath the surface of the skin and said optical components defining a return path for Raman scattered light selectively receive for communication to said light detection unit light scattered from near said measurement location such that at least 50% of Raman scattered light received at the light detection unit originates at depths from 60 to 400 μm beyond said distal surface of the skin engaging member.

The light source is preferably a laser. A preferred form of laser to use as the light source is a diode laser with a wavelength in the range of 300-1500 nm. Suitable preferred wavelengths are 785, 830, or 850 nm, 830 nm being especially preferred. A suitable power range is 50-1000 mW. For example, one may use a 830 nm, 500 mW FC-830 laser from RGB Lase.

The apparatus may include an optical probe for measuring light signals in which the optical components defining the light path from the light source to the measurement location comprise a first optical fiber guiding incoming light from said light source, a lens focusing said incoming light towards, i.e. into or onto, the measurement location. The optical components for defining a return path for Raman scattered light may comprise said lens and a distal portion of the said first optical fiber collecting altered light from the measurement location and a second optical fiber guiding the altered light to the light detection unit. However, instead of employing a second optical fiber as described, a spectrophotometer may be integrated directly into the handpiece. Optionally, there may be a further light detection unit (or light logging device) measuring intensity fluctuations in said incoming light, and this further light detection unit may advantageously be positioned after said first optical fiber, whereby said further light detection unit receives a part of said incoming light from said first fiber.

The use of optical fibers is advantageous in that although a microscope can be used, a microscope-based optical probe is not a movable object and a user's body part would be awkward to place in a position where measurements could be made. A possibility would be for the patient to insert his/her arm directly under or above the microscope objective in the microscope. Unfortunately, this is cumbersome if not impossible with most microscopes.

An optical probe employing not the whole microscope but only microscope objective(s) mounted separately on e.g. a table allows for a larger accessibility between probe and sample. Measurements of blood sugar, lactate or other metabolite levels in a patient in vivo become more convenient as the patients arm or finger can be placed in front of the microscope objective(s) without much difficulty. However, if the chosen sample is a leg, it might prove more difficult to place it appropriately in front of the microscope objective(s).

Inside the optical probe, said light logging device will normally be positioned after a dichroic mirror, which allows a minor part of the incoming light to either pass through the dichroic mirror and onto said light logging device or to be reflected by the dichroic mirror onto said light logging device. Alternatively, a splitting device can be positioned between said first fiber and said dichroic mirror, where said splitting device reflects a minor part of the incoming light onto said light logging device.

One advantage with using a light logging device is that it allows for a precise measure of the variations in the intensity of the incoming light at all material times. This ensures that variations in the intensity of the altered light due to variations in the incoming light and not sample variations can be compensated for.

In an embodiment of the invention, said lens focusing incoming light towards said sample is arranged at the surface of said optical probe such that said lens is in direct contact with the skin (213) during measuring.

An advantage with having the lens in direct contact with the skin during measurement is that the sample penetration depth, and thereby the distance from the optical probe to the sample focus point, is known exactly, as it is defined by the focal length of the lens.

In another embodiment of the invention, said optical probe further comprises a window, where said window is positioned between said lens and the skin, such that said window is in direct contact with the skin during measuring, and where the thickness of said window is smaller than the focal length of said lens.

An advantage with inserting a window between the lens and the skin is that it can provide an easier cleaning of the optical probe, if a fragile lens sensitive to cleaning is used.

Another advantage with inserting a window between the lens and the skin is that the penetration depth can be varied depending on the thickness of the window. This provides one way of setting the penetration depth to the value characterising the invention.

Equally, instead of having a solid window, a window aperture can be provided between the lens and the skin, the aperture being formed in the skin engaging member.

The optical probe according to the invention, may further comprise a dichroic mirror positioned after said first optical fiber, where said dichroic mirror reflects any percent between $re\_in=0$ and 100 (e.g. 90%) and transmits any percent between $tr\_in=0$ and 100 (e.g. 10%) of said incoming light, where $re\_in+tr\_in=100$ percent (ignoring losses), and reflects any percent between re_se=0 and 100 (e.g. 30%) and transmits any percent between tr_se=0 and 100 (e.g. 70%) of said altered light, where re_se+tr_se=100 percent (ignoring losses). Hence said dichroic mirror may reflect most of the incoming light and transmit most of the altered light.

Said dichroic mirror is normally positioned at an angle of 45 degrees in relation to the propagating direction of said incoming light out of said first optical fiber.

In an embodiment where most of the incoming light is reflected by the dichroic mirror, said light logging device may be positioned after said dichroic mirror, whereby said light logging device measures intensity fluctuations in said incoming light transmitted through said dichroic mirror.

In another embodiment where most of the incoming light is reflected by the dichroic mirror, a splitting device may be positioned between said first optical fiber and said dichroic mirror, whereby said light logging device measures intensity fluctuations in said incoming light reflected of by said splitting device.

In an embodiment of the invention, said dichroic mirror is transmitting most (e.g. ≥90%) of the incoming light whilst passing a minor portion (e.g. ≤10%) and is reflecting most of the altered light (e.g. ≥70%) whilst passing a smaller amount (e.g. ≤30%).

In an embodiment where most of the incoming light is transmitted by the dichroic mirror, said light logging device may be positioned after said dichroic mirror, whereby said light logging device measures intensity fluctuations in said incoming light reflected of by said dichroic mirror.

An advantage of having the light logging device situated directly after said dichroic mirror is that it utilizes the part of the incoming light, which is not reflected by the dichroic mirror, and otherwise would be lost. There is consequently no need for any additional optical components to be inserted inside the optical probe in order collect light for measuring of the fluctuations in the incoming light.

In one embodiment of the invention, the angle α between the direction (239) of light out of said first optical fiber (203) and the direction (241) of light entering said second optical fiber (227) is substantially α=90 degrees. The angle could also be in the range α=80-100 degrees.

In one embodiment of the invention, said optical probe further comprises at least a first aperture where said first aperture only allows altered light from the focus point in the skin to enter said second fiber thereby ensuring a confocal image, and where said first aperture is positioned immediately in front of said second fiber. Said aperture can be a separate element, but a narrow opening of said second fiber can equally well function as said aperture.

An advantage with using an optical aperture positioned before the second fiber is that the optical aperture works as a 3D depth filter eliminating optical signals generated outside of the confocal area, i.e. the sample focus spot. The advantage with using a confocal optical probe is that the altered light entering the second fiber arise solely from interactions between the incoming light and the skin at the focus spot; hence contributions from the cone-like areas above and below the focus spot are minimized or eliminated.

In another embodiment of the invention, one or more apertures can additionally be employed to obtain a sharper 3D depth image. A second aperture is preferably positioned between the skin and the lens focusing the light into the sample. This second aperture can be separate element, but a narrow opening of the optical probe at the point where light exits/is collected by the lens can equally well function as an aperture.

Although apparatus according to the invention is designed and configured for measuring optical signals in the skin in vivo, it could also be employed for measuring optical signals by immersing it into e.g. a blood sample thereby making the measurement in vitro.

Generally, the optical elements found inside an optical probe of apparatus according to the present invention are enclosed by a cover. A preferred optical probe can be moved around freely due to the use of flexible fibers for guiding light into and out of the optical probe. This enables easy in vivo measurements of e.g. blood sugar levels in a patient using different body areas such as an arm, a finger, a leg or similar. The apparatus may however be constructed so that the optical components are contained in a housing which defines a specific location on which to place a fingertip pad for performance of the measurement. The stratum corneum thickness of a fingertip pad will typically be from 10-40 µm (see Marks, James G; Miller, Jeffery (2006). Lookingbill and Marks' Principles of Dermatology (4th ed.). Elsevier Inc. Page 7. ISBN 1-4160-3185-5 and Thickness of the Stratum Corneum of the Volar Fingertips H. FRUHSTORFER, U. ABEL, C.-D. GARTHE, AND A. KNU" TTEL. Accordingly, the preferred measurement depths of 200-300 µm will be from 160 to 190 µm up to 260 to 290 µm below the stratum corneum. Depths of measurement for all skin areas are preferably from 50 to 390 µm, more preferably from 190 to 290 µm below the stratum corneum.

A primary application of the apparatus is generally to measure blood sugar or lactate levels in a patient. The level of glucose or lactate in blood correlates with the level in interstitial fluid at the selected depth.

BRIEF DESCRIPTION OF THE DRAWINGS

The invention will be further described and illustrated by reference to the accompanying drawings in which.

DESCRIPTION OF PREFERRED EMBODIMENTS

Figure 1:
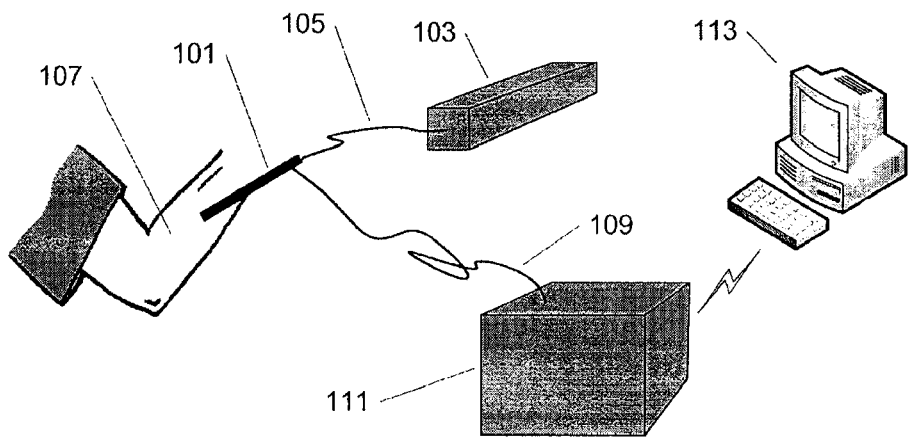
FIG. 1 shows schematically apparatus according to the invention.

FIG. 1 schematically shows apparatus according to the invention in use for measuring the concentration of glucose (or another skin substance) in vivo. An optical probe 101 receives light from a light source 103 through a first fiber 105. In this embodiment of the invention, the light source 103 is a laser. The incoming light illuminates and interacts with the skin 107. Altered light received back from the skin, is collected by the optical probe 101 and sent via a second fiber 109 to a spectrometer 111 connected to a computer 113 for subsequent analysis of the spectral components. Within the spectrophotometer 111 there is a light detection unit. Alternatively, of course, the spectrophotometer function could be built into the hand piece and corresponding electronic signals representing the spectral information may be outputted from there to the computer.

In this embodiment of the invention, the optical probe is applied to a patient's arm, but it could also be applied to a finger or another body part. Likewise, the measurement is displayed as being carried out in vivo, but the optical probe 101 could also be employed for measuring optical signals by immersing it into e.g. a blood sample thereby making the measurement in vitro.

Generally, the optical elements found inside the optical probe 101 of the apparatus according to the present invention are enclosed by a cover, where the cover has at least one opening for the two fibers 105 and 109 and an opening for the light employed to illuminate the sample. The latter opening can also be used for collecting the altered light from the sample. The optical probe 101 can be moved around freely due to the use of flexible fibers for guiding light into and out of the optical probe. This enables easy in vivo measurements of e.g. blood sugar levels in a patient using different body areas such as an arm, a finger, a leg or similar.

A primary application of the optical probe 101 is to measure blood sugar levels in a patient. The probe can however also be used for measuring e.g. the level of haemoglobin, cholesterol, alcohol and/or drug in the blood or the temperature and/or variations of the temperature in the blood.

Figure 2:
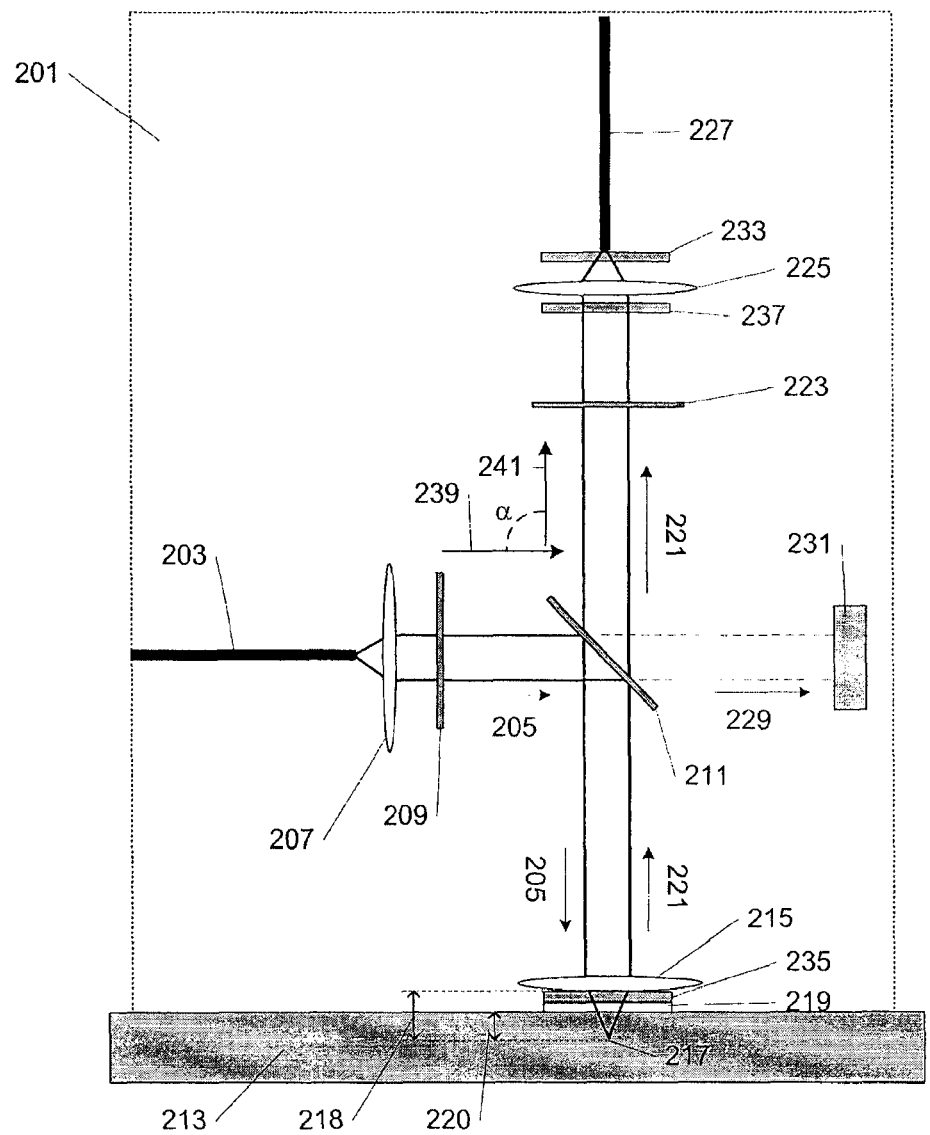
FIG. 2 shows a first embodiment of an optical probe forming part of the apparatus of FIG. 1.

FIG. 2 shows a first embodiment of the optical probe 201 comprising a first optical fiber 203 for guiding light into the optical probe 201. According to this embodiment of the invention, the light source is normally a laser. Upon exiting the first fiber 203, the incoming light 205 is collimated using a first lens 207 and optically filtrated by passing through a first filter 209 blocking any percentage between 0 and 100 of frequencies/wavelengths outside the laser frequency/wavelength. Blocking of frequencies outside the laser frequency ensures that e.g. Raman scattering generated inside the first fiber 203 is removed from the incoming light 205. The first filter 209 may also block any percentage between 0 and 100 of the laser frequency. This is an advantage if the intensity of the incoming light 205 is too high for the requirements of the sample. The first filter 209 is preferably a band-pass filter, notch filter, an edge filter or such.

The optical probe 201 further comprises a dichroic mirror 211 that either reflects or transmits any percentage between 0 and 100 of the light, where the percentage of reflected and transmitted light is dependent on the coating on the dichroic mirror 211, the angle at which the light hits the dichroic mirror 211, and the frequency of the light. The dichroic mirror 211 can e.g. be coated such that it reflects the highest percent of the incoming light 205 when the dichroic mirror 211 is positioned at a given angle in relation to the direction of the incoming light 205. Changing the angle between the dichroic mirror 205 and the incoming light 205 will therefore reduce the percent of incoming light 205 reflected by the dichroic mirror 211.

In this embodiment of the invention, most of the incoming light 205 is reflected by the dichroic mirror 211 and focused inside the skin 213 of a subject by a second lens 215. The focus point 217 of the incoming light 205 is defined by the focal length 218 of the second lens 215 and the distance distal of the lens of a window 219 and in particular its distal surface which engages the skin in use. The second lens 215 is preferably convex, but could also be aspheric or planar.

The dichroic mirror 211 is in the current embodiment positioned at an angle of 45° in relation to the propagating direction of the incoming light 205. The majority of the incoming light 205 is consequently reflected at a 90° angle. The dichroic mirror 211 could be positioned at an angle between 0-90° as well. In one embodiment of the invention, the percent of the incoming light 205 which is reflected (re_in) and transmitted (tr_in) by the dichroic mirror 211 is re_in≥90% of (re_in+tr_in) and tr_in≤10% of (re_in+tr_in).

In another embodiment of the invention, the percent of the incoming light 205 which is reflected and transmitted by the dichroic mirror 211 is re_in≥98% of (re_in+tr_in) and tr_in≤2% of (re_in+tr_in), respectively.

The illustrated optical probe 201 further comprise a thin window 219, which is positioned between the second lens 215 and the skin 213. The thickness of the window 219 is smaller than the focal length of the second lens 215, i.e. smaller than the distance from the second lens 215 to the focus point 217 inside the skin 213. The window 219 can serve to protect the second lens 215 thereby enabling easy cleaning of the optical probe 201 after it has been in contact with the skin 213. The window 219 acts as a skin engaging member and the distance from the skin engaging surface thereof to the focal point of the lens 215 determines the depth 220 below the surface of the skin at which Raman signals are generated. This is ideally set such that most of the laser light intensity is focused at 250 μm below the skin surface. If it is desired that the apparatus can be adapted for other uses, provision may be made for installing windows 219 of different thicknesses, thereby altering the sample penetration depth 220. Typical alternative sample penetration depths 220 are in the rage between 150 to 500 μm depending on the focal length 218 of the second lens 215 and the thickness of the window 219. Both shorter and longer penetrations depths 220 can also be obtained.

In another embodiment of the invention, there is no window, and the second lens 215 is in direct contact with the skin 213. The focal length of the lens for light passing through the skin will then ideally be 200-300 μm. Again, if it is desired that the apparatus can be adapted for other uses as well, the lens may be made replaceable with lenses of other focal lengths.

In addition to focusing the incoming light 205 into the skin 213, the second lens 215 collimates the altered light 221 from the focus point 217. In the current embodiment, the dichroic mirror 211 transmits the majority of the altered light 221, but reflects backscattering of the incoming light 205. This filters unwanted frequencies, i.e. the frequency of the back reflected incoming light 205, from the altered light 221 generated as a result of interactions with the skin 213.

In one embodiment of the invention, the percent of the altered light 221 which is reflected (re_se) and transmitted (tr_se) by the dichroic mirror 211 is re_se≤30% of (re_se+tr_se) and tr_se≥70% of (re_se+tr_se), respectively.

In another embodiment of the invention, the percent of the altered light 221 which is reflected and transmitted by the dichroic mirror 211 is re_se≤10% of (re_se+tr_se) and tr_se≥90% of (re_se+tr_se), respectively.

The altered light 221 is further optically filtered by passing through a second filter 223 before the light is focused by a third lens 225 into a second fiber 227. The second filter 223 is preferably a band-pass filter, a notch filter, an edge filter or such and is characterized by transmitting any percentage between 0 and 100 of the altered light 221 collected by the second lens 215 and by blocking any percentage between 0 and 100 of frequencies close or equal to the frequency of the incoming light. This can e.g. insure that the percentage of unwanted Rayleigh scattering passing through the second filter 223 is neglectable at the same time as nearly all Raman light scattered from the skin 213 are allow to pass through.

When measuring emission, such as fluorescence, it can be of interest to reduce the intensity of the light reaching a detection device, in order to avoid saturation and/or damage to the detection device. To achieve this, a second filter 223, which allows less than 100% of the emission to pass through, can be employed.

In this embodiment of the invention, the dichroic mirror 211 does not reflect all of the incoming laser light 205. Instead it allows a smaller fraction of the light 229 to pass through the dichroic mirror 211 and onto a light logging device 231, which detects the intensity and/or power of the light 229 after passing through the dichroic mirror 211. The light logging device 231 can be a photodiode, a CCD detector, a thermal transistor or a fiber guiding to such a device, or similar.

One advantage with using a light logging device 231 is that it allows for a precise measure of the variations in the intensity of the incoming light at all time. This ensures that variations in the intensity of the altered light 221 due to drift in the intensity of the laser light can be compensated for to prevent apparent glucose concentration variations that would otherwise be caused by variations in the incoming light intensity. The signal recorded by the light detection unit in the spectrophotometer is normalized using the measured value of the intensity of the primary light. The normalization may be done in software when the data is analyzed and not in real time.

Incorporating the light logging device 231 into the optical probe 201 and having it positioned after coupling the incoming light 205 out of the first fiber 203 is a clear advantage, since the process of coupling laser light into a fiber is quite sensitive to both the angle at which the laser light is focused into the fiber and the distance between the focus point of the lens, which focuses the laser into the fiber, and the fiber it self. Variations in the intensity of the light exiting the fiber will thus vary as a result of the efficiency by which the laser light is coupled into the fiber. Using a light logging device positioned between the laser and the fiber as in the previously described patents/articles will therefore not give a precise measure of the intensity variations of the light focused into the skin. However, measuring the variation in the incoming light intensity at the light source or at any point between the light source and the skin is within the invention in this and other embodiments.

In addition to the above described optical elements, the optical probe 201 may also be equipped with at least a first optical aperture 233 positioned before the second fiber 227. The first optical aperture 233 works as a 3D depth filter eliminating optical signals generated outside of the confocal area, i.e. the focus spot 217. The advantage with using a confocal optical probe is that the altered light 221 entering the second fiber 227 arise solely from interactions between the incoming light 205 and the skin 213 at the focus spot 217; hence contributions from the cone-like areas above and below the focus spot 217 are eliminated.

According to this first embodiment of the invention, the first aperture 233 is displayed as a separate element. However, a narrow opening of the second fiber 227 can equally well function as a first aperture 233.

In addition to the first aperture 233, one or more apertures can be employed to obtain a sharper 3D depth image. A second aperture 235 is preferably positioned between the second lens 215 and the skin 213. In a preferred embodiment, where there is no window 219 and the second lens 215 is convex, the second lens 215 will still be in direct contact with the skin 213 even with the thin second aperture 235 positioned between the skin 213 and the second lens 215.

In the current embodiment of the invention, the second aperture 235 is displayed as a separate element. However, a narrow opening of the optical probe 201 at the point where light exits/is collected by the second lens 215 can equally well function as a second aperture 235.

A third aperture 237 can preferably be positioned just before the third lens 225 as shown in the current figure. This can further improve the 3D depth image.

The two fibers 203 and 227 are normally arranged such that the direction 239 of the light exiting the first fiber 203 and the direction 241 of the light entering the second fiber 227 are at an angle of $\alpha=90°$ in relation to one another. Alternative arrangements of the two fibers 203 and 227 and consequently the direction of the light exiting/entering them (239 and 241, respectively) can also be found, yielding an angle $\alpha \neq 90°$.

The two fibers 203 and 227 are preferably multimode mode fibers, but could also be single mode fibers.

Figure 3:
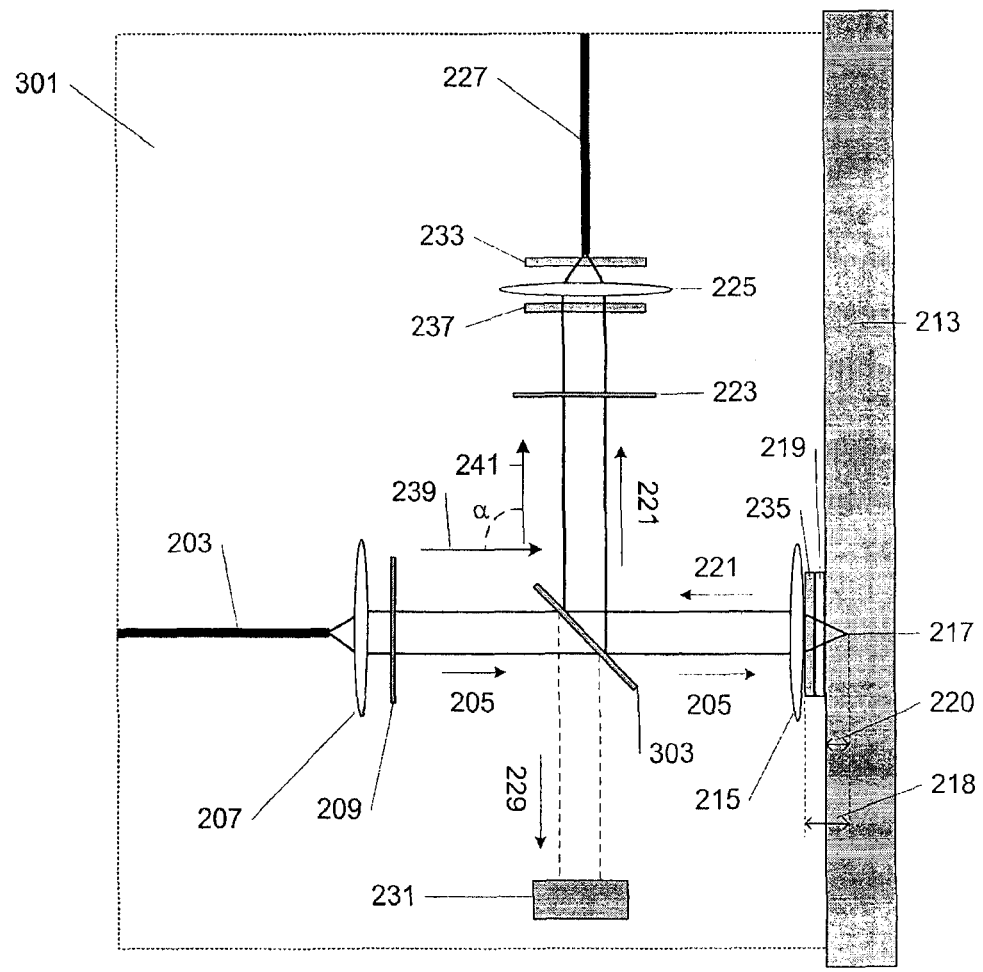
FIG. 3 shows a second embodiment of an optical probe forming part of the apparatus of FIG. 1.

FIG. 3 shows a second embodiment of the invention, where the optical probe 301 comprises a first optical fiber 203 for guiding light into the optical probe 301, a first lens 207 for collimating the incoming light 205, a first filter 209 blocking any percentage between 0 and 100 of frequencies outside the frequency of the incoming light, a second lens 215 focusing the incoming light 205 into and for collecting the altered light 221 from the skin 213, a second filter 223 for optically filtrating the altered light 221, a third lens 225 for focusing the altered light 221 into a second optical fiber 227, and a light logging device 231, which detects intensity variations in the incoming light.

The two fibers 203 and 227 are preferably multimode mode fibers, but could also be single mode fibers. The two fibers 203 and 227 are normally arranged such that the direction of the light exiting the first fiber 203 and the direction of the light entering the second fiber 227 are perpendicular in relation to one another. Alternative arrangements of the two fibers 203 and 227 and consequently the direction of the light exiting/entering them can also be found.

The two filters 209 and 223 are normally a band-pass filter, a notch filter; an edge filter or such. The second lens 215 is preferably convex, but could also be aspheric or planar.

The optical probe 301 further comprises a dichroic mirror 303 that either reflects or transmits any percentage between 0 and 100 of the light. The dichroic mirror 303 is in the current embodiment positioned at an angle of 45° in relation to the propagating direction of the incoming light 205, but could also be positioned at an angle between 0-90° as well.

According to the second embodiment of the invention, the dichroic mirror 303 allows the majority of the incoming light 205 to pass through the dichroic mirror 303 and reflects only a smaller part 229 of the incoming light which is detected by the light logging device 231. The altered light 221 is reflected by the dichroic mirror 303 at an approximate 90 degree angle.

In one embodiment of the invention, the percent of the incoming light 205 which is reflected and transmitted by the dichroic mirror 303 is $re\_in \leq 30\%$ of $(re\_in+tr\_in)$ and $tr\_in \geq 70\%$ of $(re\_in+tr\_in)$, respectively, and the percent of the altered light 221 which is reflected and transmitted by the dichroic mirror 303 is $re\_se \geq 70\%$ of $(re\_se+tr\_se)$ and $tr\_se \leq 30\%$ of $(re\_se+tr\_se)$, respectively.

In another embodiment of the invention, the percent of the incoming light 205 which is reflected and transmitted by the dichroic mirror 303 is $re\_in \leq 10\%$ of $(re\_in+tr\_in)$ and $tr\_in \geq 90\%$ of $(re\_in+tr\_in)$, respectively, and the percent of the altered light 221 which is reflected and transmitted by the dichroic mirror 303 is re_se≥90% of (re_se+tr_se) and tr_se≤10% of (re_se+tr_se), respectively.

The optical probe 301 may further optionally comprises a thin window 219 constituting a skin engaging member, which is positioned between the second lens 215 and the skin 213, a first optical aperture 233, second aperture 235 normally positioned between the second lens 215 and the skin 213, and a third aperture 237 normally be positioned just before the third lens 225. According to this second embodiment of the invention, the apertures 233 and 235 are displayed as a separate element. However, a narrow opening of the second fiber 227 can equally well function as a first aperture 233 and a narrow opening of the optical probe 301 at the point where light exits/is collected by the second lens 215 can equally well function as a first aperture 233.

The skin penetration depth 220 is again set ideally at 200 (or 210)-300 µm. It can in addition be made adjustable for other uses and again, typical sample penetration depths 220 are then in the rage between $\frac{1}{10}$-3 mm depending on the focal length 218 of the second lens 215 and the thickness of the window 219, if such is part of the optical probe 301. Both shorter and longer penetrations depths 220 can also be obtained.

The advantages with the optical probe 301 are the same as the ones described in relation to the optical probe 201 shown in FIG. 2.

Figure 4:
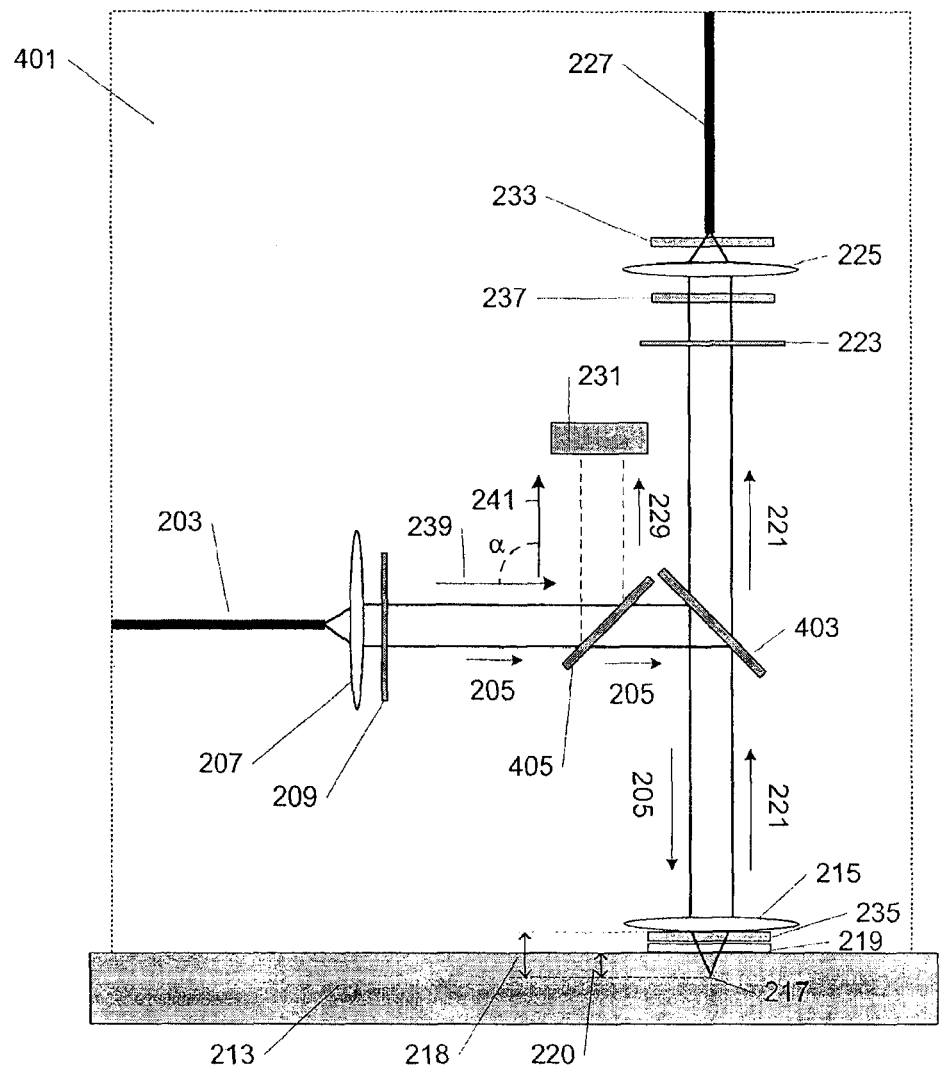
FIG. 4 shows a third embodiment of an optical probe forming part of the apparatus of FIG. 1.

FIG. 4 shows a third embodiment of the invention, where the optical probe 401 comprises a first optical fiber 203 for guiding light into the optical probe 301, a first lens 207 for collimating the incoming light 205, a first filter 209 blocking any percentage between 0 and 100 of frequencies outside the frequency of the incoming light, a second lens 215 focusing the incoming light 205 into and for collecting the altered light 221 from the skin 213, a second filter 223 for optically filtrating the altered light 221, a third lens 225 for focusing the altered light 221 into a second optical fiber 227, and a light logging device 231, which detects intensity variations in the incoming light.

The two fibers 203 and 227 are preferably multimode mode fibers, but could also be single mode fibers. The two fibers 203 and 227 are normally arranged such that the direction of the light exiting the first fiber 203 and the direction of the light entering the second fiber 227 are perpendicular in relation to one another. Alternative arrangements of the two fibers 203 and 227 and consequently the direction of the light exiting/entering them can also be found.

The two filters 209 and 223 are normally a band-pass filter, a notch filter, an edge filter or such. The second lens 215 is preferably convex, but could also be aspheric or planar.

The optical probe 401 further comprises a dichroic mirror 403 that either reflects or transmits any percentage between 0 and 100 of the light. The dichroic mirror 403 is in the current embodiment positioned at an angle of 45° in relation to the propagating direction of the incoming light 205, but could also be positioned at an angle between 0-90° as well.

According to the third embodiment of the invention, the dichroic mirror 403 reflects the majority of the incoming light 205 in a 90 degree angle onto the skin 213 and allows for the altered light 221 to pass through. In contrary to the first and the second embodiments, the smaller part 229 of the incoming light, which is used for light logging, is not collected after passing through or being reflected by the dichroic mirror 403. Instead, an optical splitting device 405 positioned between the first filter 209 and the dichroic mirror 403 is employed to direct a smaller fraction 229 of the incoming light onto the light logging device 231. The splitting device 405 can be a beam splitter, a dichroic mirror allowing most of the incoming light to pass through, a low density filter or similar.

In one embodiment of the invention, the percent of the incoming light 205 which is reflected and transmitted by the dichroic mirror 403 is re_in≥90% of (re_in+tr_in) and tr_in≤10% of (re_in+tr_in), respectively, and the percent of the altered light 221 which is reflected and transmitted by the dichroic mirror 403 is re_se≤10% of (re_se+tr_se) and tr_se≥90% of (re_se+tr_se), respectively.

The optical probe 401 may further optionally comprises a thin window 219, which is positioned between the second lens 215 and the skin 213, a first optical aperture 233, second aperture 235 normally positioned between the second lens 215 and the skin 213, and a third aperture 237 normally be positioned just before the third lens 225. According to this second embodiment of the invention, the apertures 233 and 235 are displayed as a separate element. However, a narrow opening of the second fiber 227 can equally well function as a first aperture 233 and a narrow opening of the optical probe 201 at the point where light exits/is collected by the second lens 215 can equally well function as a first aperture 233.

Typical sample penetration depths 220 are in the rage between $\frac{1}{10}$-3 mm depending on the focal length 218 of the second lens 215 and the thickness of the window 219, if such is part of the optical probe 401. Both shorter and longer penetrations depths 220 can also be obtained.

The advantages with the optical probe 401 are the same as the ones described in relation to the optical probe 201 shown in FIG. 2.

The optical probes 201, 301, and 401 are all constructed such that the optical elements inside are positioned in very close proximity to one another, and the FIGS. 2-4 are only meant as illustrations and do not show the accurate distances between the different optical elements.

An advantage of placing the optical elements inside the optical probe in as close proximity as possible, is that this feature enhances both the intensity of the incoming light at the sample focus point and the efficiency by which the altered light is collected, since effects from diffraction of the incoming light and/or the altered light is diminished.

EXAMPLES

Figure 5:
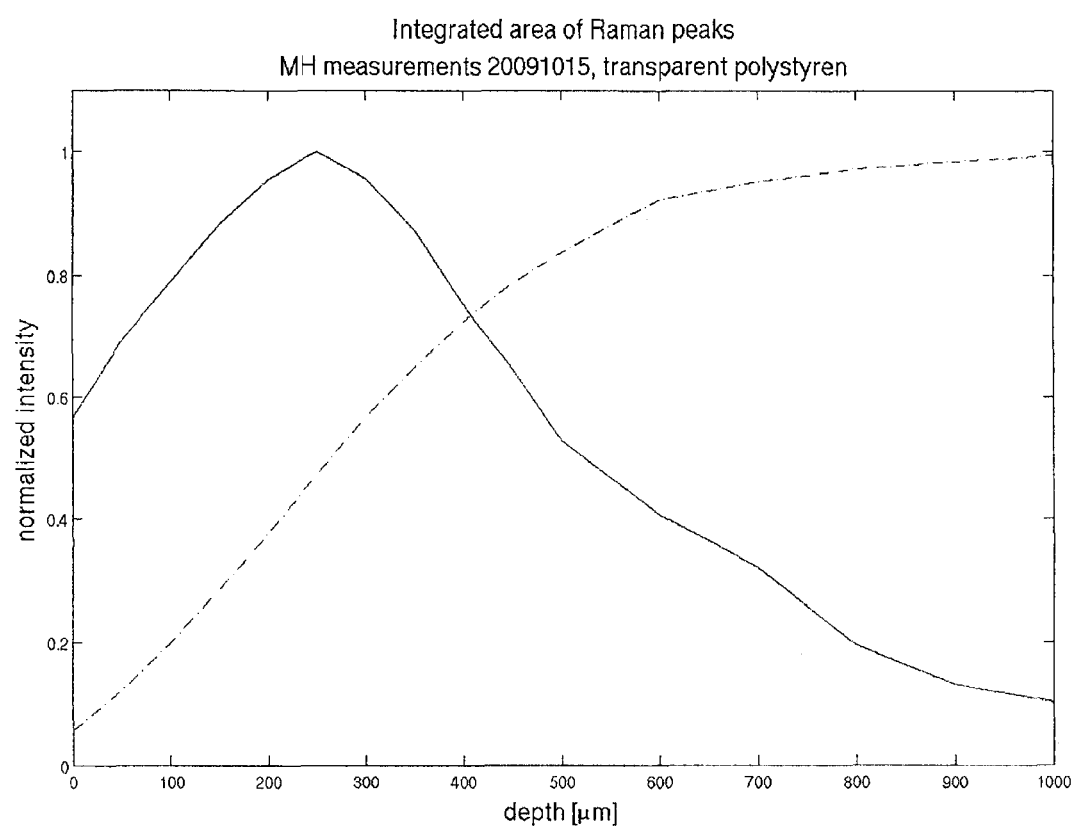
FIG. 5 shows the depth distribution of Raman scattering found using a focusing depth in accordance with the invention.

Apparatus as described above with reference to FIG. 2 was set to focus its output of light to a depth of approximately 250 µm beyond the surface of a polystyrene sample to which the window 219 was applied. FIG. 5 shows a depth profile of the origin of the Raman scattered light received back at the detector. It may be observed that the largest signal intensity is derived from the depth to which the light was focused. About 15% of the received signal originates from between 200 and 300 µm beyond the surface and somewhat more than 60% of the recovered signal originates between 60 and 400 µm beyond the surface. The depth profiles were measured using a thin (approximately 200-220 µm) transparent polystyrene material. The lens of the apparatus is placed directly against this to collect signals from a depth of 0 and the material is moved progressively away from the lens in steps of 50 µm to collect Raman signals from further distances. The depth profiles are calculated as the integrated area of the polystyrene peaks—baseline corrected. The depth profiles are then plotted as a normalized version of the integrated Raman signal area for each step.

More than 90% of the received signal originates from a depth of less than 600 µm. Whilst less than 20% of the signal originates from depths of less than 100 µm.

Figure 6:
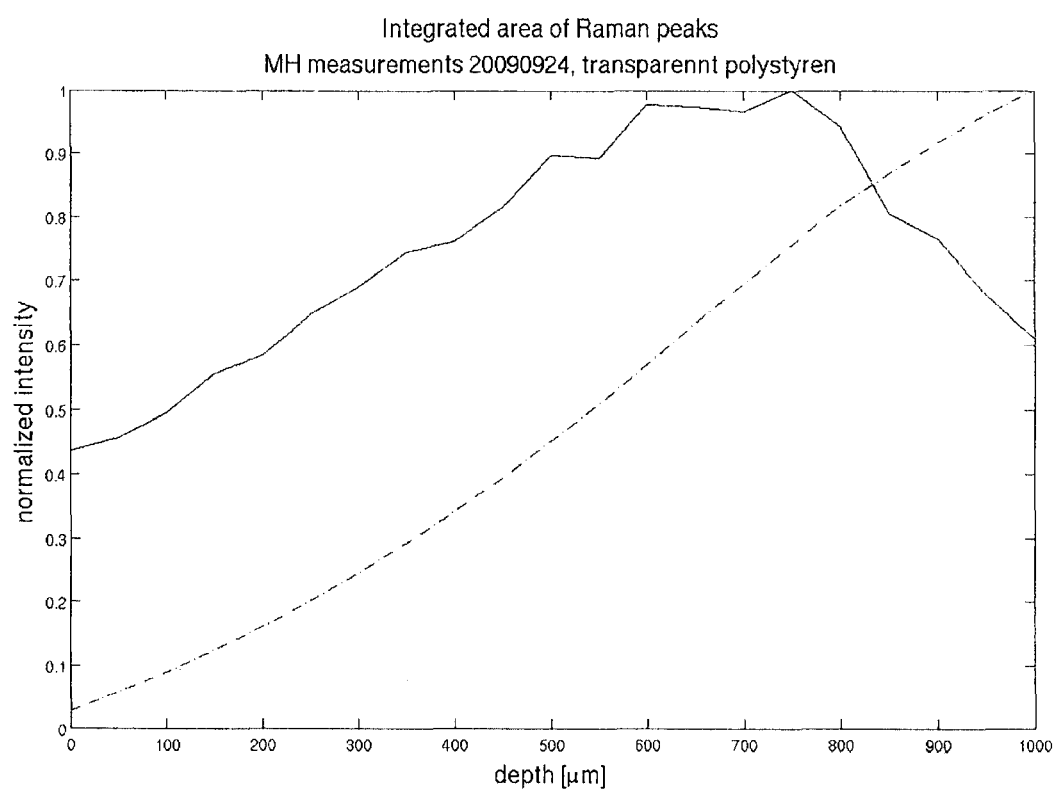
FIG. 6 shows the depth distribution of Raman scattering using a focusing depth which is too large.
Figure 7:
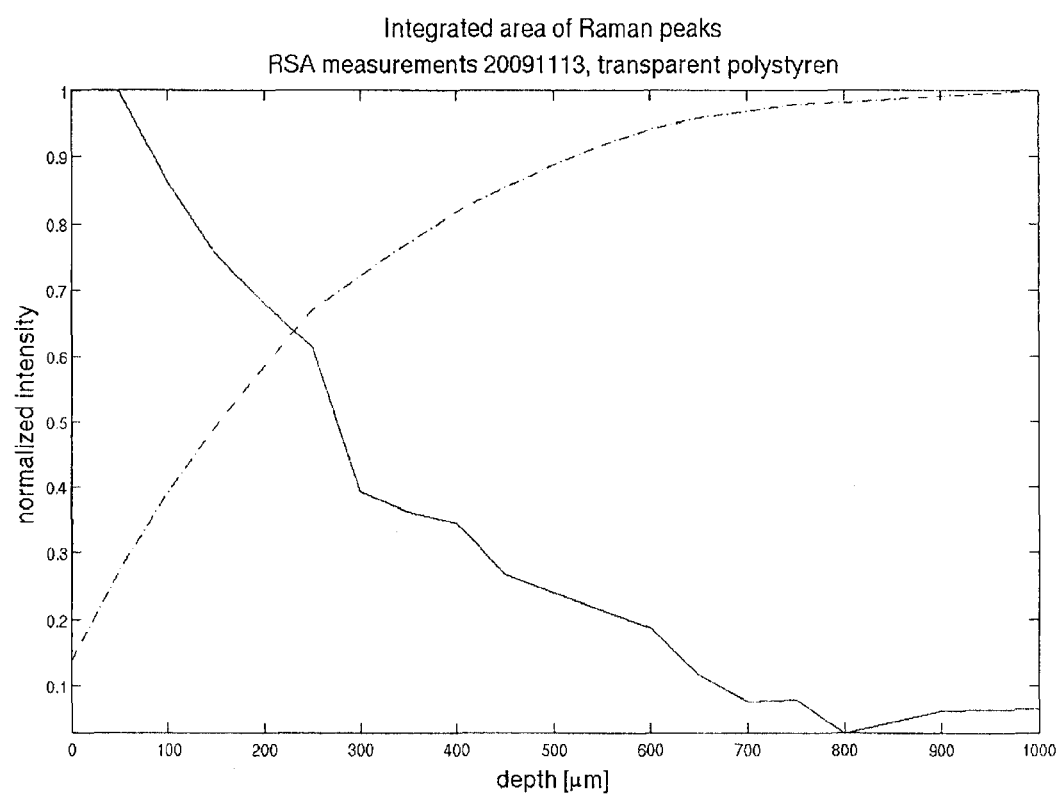
FIG. 7 shows the depth distribution of Raman scattering using a focusing depth which is too small.

For comparison, the apparatus was adjusted to focus the applied light to a depth of approximately 750 μm below the surface and a corresponding depth profile was obtained which is shown in FIG. 6. The apparatus was further adjusted to focus the applied light immediately below the surface and a corresponding depth profile was obtained which is shown in FIG. 7.

The apparatus adjusted in each of these three ways was used to make glucose measurements on volunteers. It was found not to be possible to make measurements with the focus set to the surface as this caused an unpleasant burning feeling.

Figure 8:
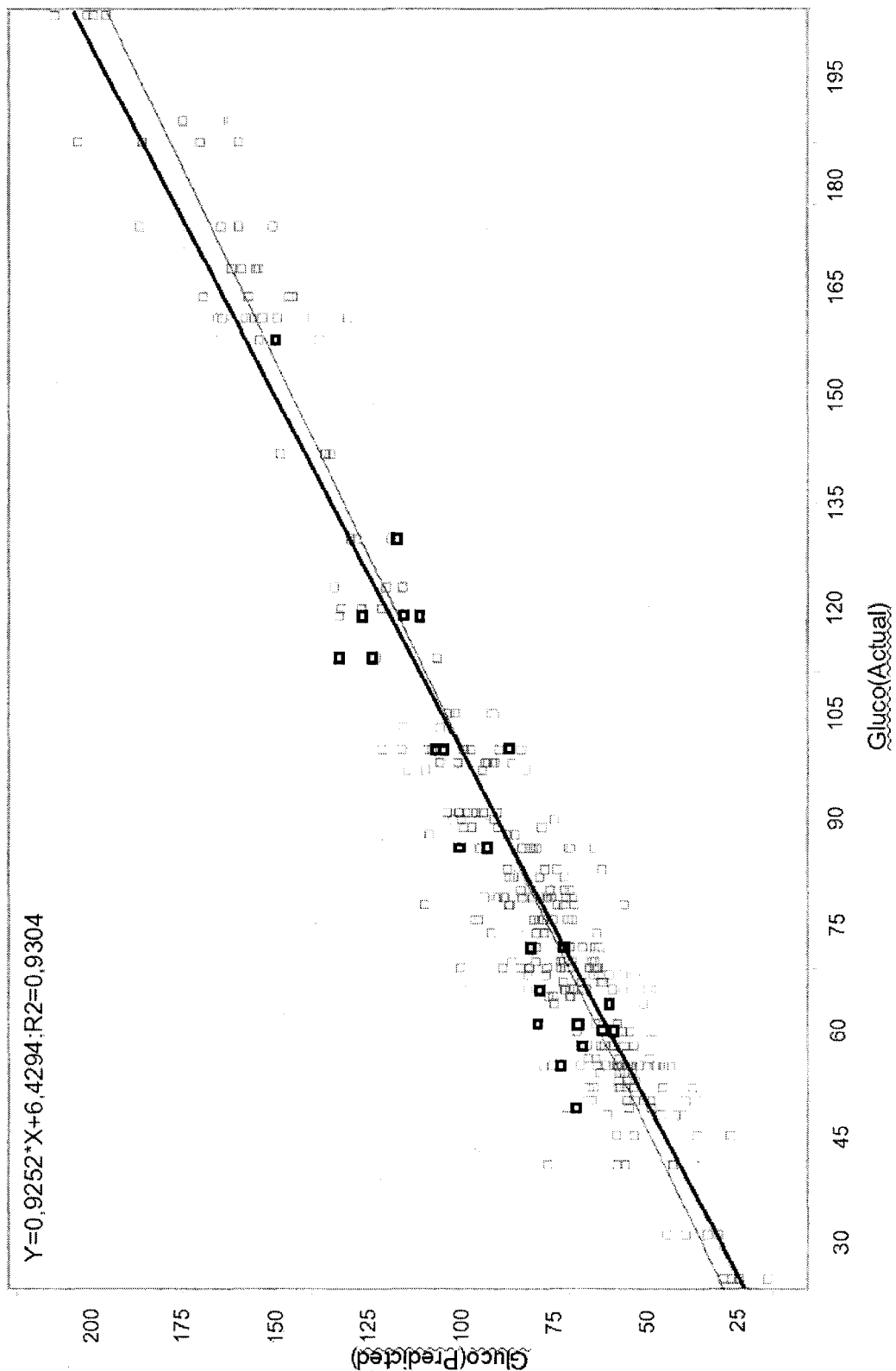
FIG. 8 shows predicted glucose measurements obtained according to the invention and actual blood glucose levels.
Figure 9:
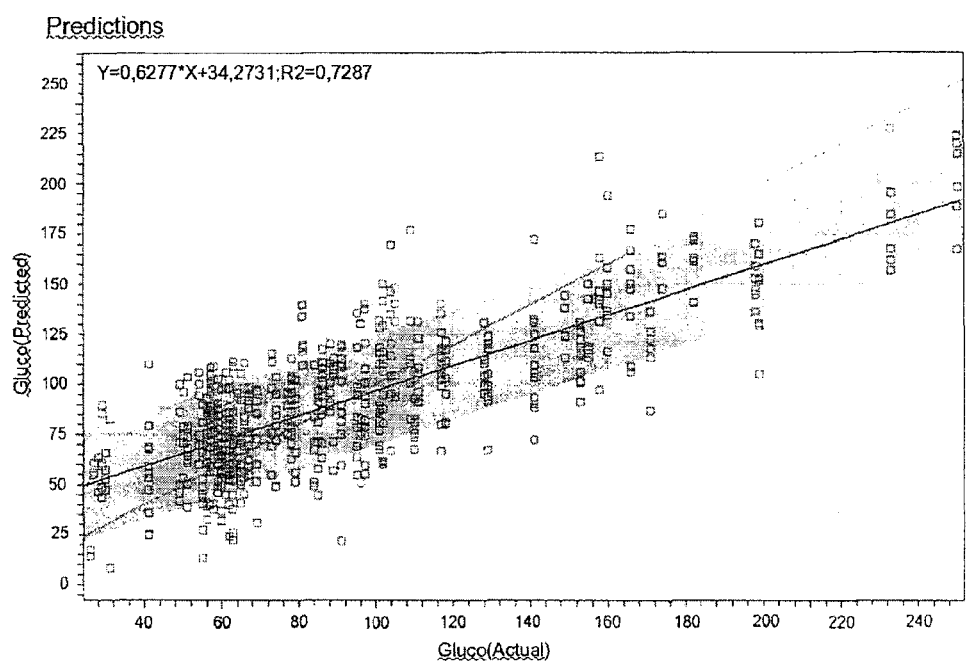
FIG. 9 shows predicted glucose measurements obtained using a focusing depth that is too large and actual blood glucose levels.

A plot of readings obtained with a focus depth of 250 μm in accordance with the invention is shown in FIG. 8, whilst readings obtained at a focus depth of 750 μm are shown in FIG. 9.

From 4-6 sequential optical measurements were made on each patient. These are plotted on the vertical axis as predicted glucose values against corresponding measurements of actual glucose level on the horizontal axis measured with Hemocue 201+ Meter as reference.

The device was calibrated for a set of patients and the same calibration was maintained for all subsequent patients.

A comparison of FIGS. 8 and 9 shows that the correlation obtained at 250 μm is far superior. Furthermore, whereas the normal expectation with apparatus for measuring glucose levels through the skin is that the apparatus will need external calibration for each patient against a glucose level measured independently, for instance by chemical analysis of blood, here it is found that a calibration performed for a set of patients may be applied to other patients and will remain good over several days, weeks or months. Indeed, unless some part of the apparatus is altered, the calibration should remain good indefinitely. Thus, the invention provides improved retention of correct calibration and transferability of calibration between individual subjects.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

101: Optical probe
103: Light source, e.g. a laser
105: First fiber
107: Sample, i.e. a patients arm
109: Second fiber
111: Spectrometer
113: Computer
201: Optical probe according to the first embodiment
203: First fiber
205: Incoming light
207: First lens
209: First filter
211: Dichroic mirror
213: Sample
215: Second lens
217: Focus point
218: Focal length of the first lens
219: Window
220: Penetration depth
221: Altered light
223: Second filter
225: Third lens
227: Second fiber
229: Minor part of the incoming light used for light logging
231: Light logging device
233: First aperture
235: Second aperture
237: Third aperture
301: Optical probe according to the second embodiment
303: Dichroic mirror
401: Optical probe according to the third embodiment
403: Dichroic mirror
405: Optical splitting device

The invention claimed is:

1. A method for non-invasive in vivo measurement by Raman spectroscopy of glucose present in interstitial fluid in the skin of a subject, comprising directing light from a light source into the skin via optical components defining a light path from said light source to a measurement location in the skin at a depth located at from 200 to 300 μm beneath the surface of the skin, receiving Raman scattered light back from the skin at a light detection unit via optical components defining a return path including using a skin engaging member having a distal surface for defining the position of said optical components defining the return path with respect to a surface of said skin and using said optical components defining a return path for Raman scattered light to transmit selectively to said light detection unit Raman scattered light scattered from near said measurement location of which at least 50% originates at depths from 60 to 400 μm beyond said distal surface of the skin engaging member, and deriving a measurement of glucose concentration at said measuring location from the Raman scattered light received at the light detection unit.

2. A method as claimed in claim 1, wherein the percentage of light transmitted by said optical components defining a return path for Raman scattered light that originates at a range of depths 60 to 400 μm beyond said distal surface of the skin engaging member, is at least 55%.

3. A method as claimed in claim 2, wherein the percentage of Raman scattered light transmitted by said optical components acting to transmit to said light detection unit light scattered from near said measurement location that originates at depths less than 600 μm beyond said distal surface of the skin engaging member is at least 90%.

4. A method as claimed in claim 1, wherein said light source is a substantially monochromatic light source emitting a wavelength selected from the group consisting of 785, 830, and 850 nm.

5. A method as claimed in claim 1, performed using a hand piece for application to the skin containing components defining said measurement location in use, and one or more optical fibres connecting said hand piece to said light source and to a processing unit containing electronic circuitry for analysis of signals received from said light detection unit to provide said measurement therefrom.

6. A method as claimed in claim 1, wherein the optical components defining a light path from said light source to a measurement location and the skin engaging member are configured such that the position distal of the skin engaging member, at which the light emitted from the light source is focused, is adjustable.

7. A method as claimed in claim 1, wherein the optical components defining a light path from said light source to a measurement location and the skin engaging member are configured such that the position distal of the skin engaging member, at which the light emitted from the light source is focused of said measurement location, is fixed.

* * * * *